United States Patent
Shishikura et al.

(10) Patent No.: US 7,910,575 B2
(45) Date of Patent: Mar. 22, 2011

(54) PROPHYLACTIC OR THERAPEUTIC AGENTS FOR ALLERGIC OPHTHALMIC DISEASES OR ALLERGIC NASAL DISEASES, COMPRISING TRICYCLIC TRIAZOLOBENZAZEPINE DERIVATIVE

(75) Inventors: Takashi Shishikura, Yokohama (JP); Tsuneyoshi Inaba, Kanagawa-Ken (JP); Yukari Hoshina, Ebina (JP); Hirotomo Akabane, Kawasaki (JP); Mitsuhiro Uchida, Kawasaki (JP)

(73) Assignee: Meiji Seika Kaisha, Ltd., Tokyo-To (JP)

( * ) Notice: Subject to any disclaimer, the term of this patent is extended or adjusted under 35 U.S.C. 154(b) by 0 days.

(21) Appl. No.: 12/224,594

(22) PCT Filed: Mar. 2, 2007

(86) PCT No.: PCT/JP2007/054008
§ 371 (c)(1),
(2), (4) Date: Sep. 2, 2008

(87) PCT Pub. No.: WO2007/100079
PCT Pub. Date: Sep. 7, 2007

(65) Prior Publication Data
US 2009/0012058 A1    Jan. 8, 2009

(30) Foreign Application Priority Data

Mar. 2, 2006  (JP) ................................. 2006-055706
Mar. 2, 2006  (JP) ................................. 2006-055711

(51) Int. Cl.
*A01N 43/00* (2006.01)
*A01N 43/04* (2006.01)

(52) U.S. Cl. ........................................ 514/183; 514/27

(58) Field of Classification Search .................. 514/163
See application file for complete search history.

(56) References Cited

U.S. PATENT DOCUMENTS

| 4,477,464 | A  | * | 10/1984 | Slade et al. ............ 514/211.04 |
| 5,686,442 | A  |   | 11/1997 | Ohtsuka et al. |
| 5,840,895 | A  |   | 11/1998 | Ohtsuka et al. |
| 6,093,714 | A  |   | 7/2000  | Ohtsuka et al. |
| 6,372,735 | B1 | * | 4/2002  | Ohtsuka et al. ......... 514/212.06 |
| 2005/0020579 | A1 |   | 1/2005  | Kitahara et al. |
| 2005/0130955 | A1 |   | 6/2005  | Ishikura et al. |

FOREIGN PATENT DOCUMENTS

| WO | 95/18130 | 7/1995 |
| WO | 97/00258 | 1/1997 |
| WO | 99/16770 | 4/1999 |
| WO | 03/055886 | 7/2003 |
| WO | 2004/113343 | 12/2004 |

OTHER PUBLICATIONS

0' Hollaren, M. (The Development and Prevention of Allergic Disease, Medscape Allergy and Clinical Immunology, 2004, printed pp. 1-5.*
International Search Report issued May 29, 2007 in the International (PCT) Application PCT/JP2007/054008 of which the present application is the U.S. National Stage.
International Preliminary Report on Patentability together with translation of PCT Written Opinion for International (PCT) Application PCT/JP2007/054008 of which the present application is the U.S. National Stage.

* cited by examiner

*Primary Examiner* — Sreeni Padmanabhan
*Assistant Examiner* — Timothy E Betton
(74) *Attorney, Agent, or Firm* — Wenderoth, Lind & Ponack, L.L.P.

(57) ABSTRACT

The present invention provides a pharmaceutical composition for use in the prophylaxis or treatment of allergic ophthalmic diseases or allergic nasal diseases, which comprises 7,8-dimethoxy-4(5H),10-dioxo-1H-1,2,3-triazolo[4,5-c][1]benzazepine, 2-(1-isopropoxycarbonyloxy-2-methylpropyl)-7,8-dimethoxy-4(5H),10-dioxo-2H-1,2,3-triazolo[4,5-c][1]benzazepine or a pharmaceutically acceptable salt thereof. The pharmaceutical composition according to the present invention has few side effects, exerts strong prophylactic and therapeutic effects in the late phase exhibiting pharmaceutical resistance to conventional instillations, and can be used appropriately for topical applications.

10 Claims, No Drawings

PROPHYLACTIC OR THERAPEUTIC AGENTS FOR ALLERGIC OPHTHALMIC DISEASES OR ALLERGIC NASAL DISEASES, COMPRISING TRICYCLIC TRIAZOLOBENZAZEPINE DERIVATIVE

CROSS-REFERENCE TO RELATED APPLICATIONS

This application is based upon and claims the benefit of priority from the prior Japanese Patent Applications No. 055706/2006 (filing date: Mar. 2, 2006) and No. 055711/2006 (filing date Mar. 2, 2006), the entire contents of which are incorporated herein by reference.

BACKGROUND OF THE INVENTION

1. Field of the Invention

The present invention provides a prophylactic or therapeutic agent for allergic ophthalmic diseases or allergic nasal diseases, comprising a tricyclic triazolobenzazepine derivative. More particularly, the present invention provides a pharmaceutical composition for use in the prophylaxis or treatment of allergic ophthalmic diseases or allergic nasal diseases, comprising 7,8-dimethoxy-4(5H),10-dioxo-1H-1,2,3-triazolo[4,5-c][1]benzazepine, a prodrug thereof, or a pharmaceutically acceptable salt thereof.

2. Background Art

Allergic ophthalmic diseases are symptoms related to eyes and their peripheral tissues based on an allergic reaction induced by various stimulations such as an immunoreaction. Specific examples thereof include seasonal allergic conjunctivitis, chronic allergic conjunctivitis, vernal conjunctivitis, atopic keratoconjunctivitis, and giant papillary conjunctivitis. Among them, the pathologic condition of the allergic conjunctivitis is mainly an inflammatory disease of conjunctiva/cornea based on type I allergic reaction. The type I allergic reaction is biphasic reaction comprising early phase (immediate-type reaction) and late phase (delay-type reaction).

The early phase appears 15 to 30 min after the exposure of antigen and disappears 1 to 2 hr after that. The late phase appears 6 to 12 hr after the disappearance of the early phase and continues for 24 to 48 hr (see Hansen I. et al.: Mediators of inflammation in the early and the late phase of allergic rhinitis. Curr. Opin. Allergy Clin. Immunol. 4; 159-163, 2004). In the early phase, symptoms such as itching, dacryorrhea, hyperemia, and conjunctiva and palpebral edema appear through the action of chemical transmitters such as histamine released from mast cells. On the other hand, the late phase is a persistent inflammation reaction induced by the invasion of inflammatory cells such as T cells and eosinophils, cytokines/chemokines produced therefrom, and toxic proteins released from the eosinophils. The late phase is considered to participate in increased severity and procrastination of the pathologic condition (see Azuma Kozue, Ohno Shigeaki: Arerugisei Ketsumaku Shikkan Gaisetsu (Outline of allergic conjunctival diseases) "NEW MOOK Ganka (Opthalmology); Arerugisei Gan Shikkan (Allergic ophthalmic diseases) 6," edited by Ohno Shigeaki et al., KANEHARA & Co., LTD., 1-5, 2003).

For the early phase, cromoglycate, an inhibitor of histamine release, and antihistamines are effective (see King H. C.: Pharmacotherapy of allergic rhinitis. in "Allergy in ENT Practice The basic guide 2nd" ed. by King H. C. et al. Thieme Medical Publisher, Inc. 178-204, 2005). On the other hand, the late phase is induced, for example, by cytokines/chemokines and toxic proteins in addition to histamine (see Kramer M. F. et al.: Nasal IL-16 and MIP-1α in late-phase allergic response. Allergy and Asthma Proc. 22; 127-132, 2001; Economides A and Kaliner M. A.: Chapter 5 Allergic rhinitis. in "Current Review of Rhinitis" ed by Kaliner M. A. Current Medicine, Inc. 35-51, 2002). These play a main role in the inflammation in the late phase. In this connection, there is a report that even levocabastine, which is the most potent antihistamine agent, cannot inhibit the late phase (see Hingorani M. and Lightman S.: Ocular Allergy in "Allergy and Allergic Diseases" ed by A. B. Kay Blackwell Science, Inc. 1645-1670, 1997).

Steroids have a potent cytokine/chemokines production inhibitory activity and a very potent effect against the late phase (see Ciprandi G. B et al.: Defrazacort protects against late-phase but early-phase reactions induced by the allergen-specific conjunctival provocation test. Allergy 48; 421-430, 1993). The steroids, however, has a risk of side effects such as cause increased ocular pressure and onset of glaucoma. Accordingly, short-term use thereof is recommended. Further, a check on the side effect by ocular specialist physicians should also be periodically carried out (see Takamura Etsuko: Arerugisei Ketsumaku Shikkan No Meno Kayumi No Seiin To Chiryo (Cause and treatment of ocular itching in allergic conjunctivitis. Allergology 19; 444-449, 2005; Barney N. P. and Graziano F. M.: Allergic and immunological diseases of eye, in Middleton's Allergy principles & practice 6th edition ed. by Adkinson N. F. et al. Mosby, Inc. 1599-1617, 2003). Accordingly, there are many restrictions in the use of steroids in allergic ophthalmic diseases, and, thus, the use of the steroids is troublesome.

Thus, the development of pharmaceutical preparations for treating and preventing allergic ophthalmic diseases, which is also effective in late phase and has no side effect, has been still desired.

Allergic nasal diseases are symptoms related to nose and its surrounding tissues based on an allergic reaction caused by various stimulations such as an immunoreaction. Specific examples thereof include seasonal allergic rhinitis, perennial allergic rhinitis, and allergic sinusitis. The clinical condition of the allergic rhinitis is also based on a type-I allergic reaction.

In the early phase of the type-I allergic reaction, for example, sneezing, itching, rhinorrhea, and edema of nasal mucosa appear due to chemical mediators such as histamine released from mast cells. Also in the early phase, as in the case of ophthalmic diseases, cromoglycate, an inhibitor of histamine release, and antihistamines are effective. In the late phase, however, in addition to histamine, cytokines/chemokines and toxic proteins produced by infiltrated inflammatory cells, such as T cells and eosinophils, induce the above symptoms. Accordingly, it is reported that any satisfactory effect cannot be attained by merely blocking the action of histamine (see Bensch G. W. et al.: Evaluation of cytokines in nasal secretions after nasal antigen challenge: lack of influence of antihistamines. Ann. Allergy Asthma immunol. 88; 457-462, 2002). The late phase is considered to participate in increased severity and procrastination of the pathologic condition, and, in fact, internal medicines of antihistamine agents are widely used as basic prescribed medicines for rhinitis. It is reported that additional administration of a nasal drop of an antihistamine agent to a patient suffering from rhinitis, however, does not improve the effect (see Bereger W. E. et al.: Efficacy of azelastine nasal spray in patients with an unsatisfactory response to loratadine. Ann. Allergy Asthma Immunol. 91; 205-211, 2003; LaForce C. F. et al.: Efficacy of azelastine nasal spray in seasonal allergic rhinitis patients who remain symptomatic after treatment with fexofenadine. Ann. Allergy Asthma Immunol. 93; 154-159, 2004). This supports the fact that the symptom induced by inflammatory cells invaded in the late phase cannot be suppressed by the antihistamine agent without difficulties.

Steroids have a potent cytokine/chemokine production inhibitory activity and exhibit a highly potent effect against the late phase in an allergic reaction of an allergic rhinitis (see Drain K. L. and Li J. T. C.: chapter 17 Corticosteroids and their use in rhinitis. in "Current Review of Rhinitis" ed. by Kaliner M. A. Current Medicine, Inc. 163-173, 2002). Regarding the clinical effect in the rhinitis as well, steroids have been confirmed to surpass antihistamine agents (see Schleimer R. P. et al.: glucocorticoids in "Middleton's Allergy Principles & Practice Sixth edition" ed by Adkinson Jr. N. F. et al Mosby, Inc. 870-913, 2003). The steroids, however, sometimes induce local side effects in noses such as nasal bleeding, local stimulation, and drying (see the above-described Drain K. L. and Li J. T. C.: chapter 17 Corticosteroids and their use in rhinitis. in "Current Review of Rhinitis" ed by Kaliner M. A. Current Medicine, Inc. 163-173, 2002). In patients who suffers from an allergic disease complicated by other allergic diseases such as asthma and atopic eczema and already use steroids, in some cases, the addition of a nasal steroid sometimes causes excessive exposure to the steroid and increases a risk of the systemic side effect (inhibition in hypothalamus-hypophysis-adrenal system and inhibition of the growth in early adolescence). For these reasons, there are many restrictions in the use of steroids in allergic nasal diseases.

Accordingly, the development of pharmaceutical preparations for treating and preventing allergic nasal diseases, which are also effective in the late phase, is less likely to cause side effect and, have still been desired in the art.

7,8-Dimethoxy-4(5H),10-dioxo-1H-1,2,3-triazolo[4,5-c][1]benzazepine (hereinafter referred to as "compound A") is a compound having the following structure and is known to have antiallergic activity (see WO 95/18130 (Japanese Patent No. 3290664 and U.S. Pat. No. 5,686,442).

(Compound A)

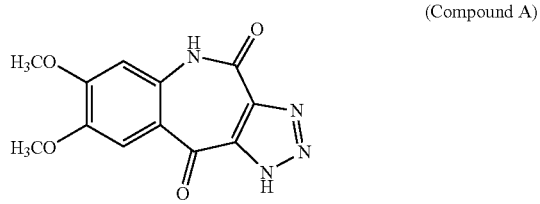

This document (the above-described WO 95/18130), however, relates to effective ingredients in oral preparations (tablets and capsules) for preventing allergic diseases. In fact, pharmacological test examples show only the prophylactic effect on the inhibition of an allergic reaction by the oral administration of tricyclic benzazepine derivatives containing compound A. Specifically, the document discloses the prophylactic effect on the inhibition of an allergic reaction in the skin of the foot by orally administering a tricyclic benzazepine derivative before the onset of the allergic reaction. Further, the document describes that the onset inhibitory effect (inhibition ratio) is about 50%.

As described above, cromoglycate, which inhibits the release of histamine, is effective in the early phase of the allergic reaction. The following fact, however, should be noted. The cromoglycate, when administered before exposure to an antigen, is effective, but on the other hand, after the induction of the allergic reaction, the effect disappears. Accordingly, the cromoglycate has been regarded as having such a property that the onset of action is slow and the action is moderate. On the other hand, the clinical judgment is such that, since the treatment is started in a symptomatic state, a satisfactory clinical effect cannot be expected by mere prophylactic effect without difficulties. Thus, the development of therapeutic effect, upon the administration of a medicament after the onset of the allergic reaction, is very important.

2-(1-Isopropoxycarbonyloxy-2-methylpropyl)-7,8-dimethoxy-4(5H),10-dioxo-2H-1,2,3-triazolo[4,5-c][1]benzazepine (hereinafter often referred to as "compound B") is a prodrug of compound A and has the following structure. It is known that compound B, after passage through mucous membranes of digestive tracts, is converted to compound A in vivo and develops antiallergic action as its drug efficacy. It has been demonstrated that compound B, as compared with compound A, can improve the absorption upon oral administration by a factor of seven (see WO 99/16770 (Japanese Patent No. 3188482 and U.S. Pat. No. 6,372,735).

(Compound B)

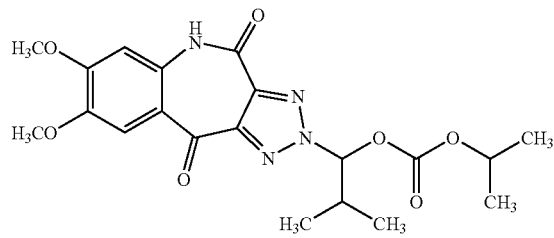

This document (the above-described WO 99/16770), however, also relates to active ingredients of oral preparations for preventing allergic diseases, and only oral preparations such as tablets and fine subtilaes are disclosed as formulation examples. Further, pharmacological test examples disclosed in the document also relate to oral preparations.

In general, it cannot be necessarily said that, even when an active ingredient is absorbed into the living body through mucous membranes, for example, in digestive tracts and exhibits an excellent effect, an excellent effect favorably comparable with the oral administration can be attained in parenteral administration. For example, when a parenteral preparation is topically administered to mucous membranes in target organs of allergic diseases, the contemplated active ingredient acts directly on the affected part. Accordingly, a lot of consideration should be placed on the dose and dosage form. Further, the possibility of side effects caused by direct action is also not negligible. In general, these matters should be studied separately from the finding in the oral administration.

SUMMARY OF THE INVENTION

The present inventors have now made a search for pharmaceutical preparations which are effective in preventing and treating allergic ophthalmic diseases or allergic nasal diseases and do not develop significant side effects. As a result, it has been found that the late phase could be substantially completely inhibited by topically administering compound A to an eye or a nose before the onset of allergic reaction (that is, for prophylactic purposes). It has also been found that the late phase can also be potently inhibited by topically administering compound A to an eye or a nose during the progression of allergic inflammation (that is, for therapeutic purposes). Further, it has been found that compound B, which is converted to compound A in vivo, has the same effect as compound A and thus is usable. The present invention is based on these finding.

Accordingly, an object of the present invention is to provide a pharmaceutical preparation, which is effective in preventing and treating allergic ophthalmic diseases or allergic nasal diseases and, at the same time, develops few side effects and is suitable for topical administration.

According to the present invention, there is provided a pharmaceutical composition for use in the prophylaxis or treatment of allergic ophthalmic diseases or allergic nasal diseases, which comprises 7,8-dimethoxy-4(5H),10-dioxo-1H-1,2,3-triazolo[4,5-c][1]benzazepine (compound A), a prodrug thereof, or a pharmaceutically acceptable salt thereof.

According to the present invention, there is also provided a pharmaceutical composition for use in the prophylaxis or treatment of allergic ophthalmic diseases or allergic nasal diseases, which comprises 2-(1-isopropoxycarbonyloxy-2-methylpropyl)-7,8-dimethoxy-4(5H),10-dioxo-2H-1,2,3-triazolo[4,5-c][1]benzazepine (compound B) or a pharmaceutically acceptable salt thereof. Compound B is a prodrug of compound A.

In a preferred embodiment of the present invention, the prophylactic or therapeutic pharmaceutical composition is administered as ocular instillation. In another preferred embodiment of the present invention, the prophylactic or therapeutic pharmaceutical composition is administered as nasal drops.

In a more preferred embodiment of the present invention, the prophylactic or therapeutic pharmaceutical composition further comprises a pharmaceutically acceptable carrier.

According to the present invention, there is further provided a method for the prophylaxis or treatment of allergic ophthalmic diseases or allergic nasal diseases, which comprises administering a prophylactically or therapeutically effective amount of 7,8-dimethoxy-4(5H),10-dioxo-1H-1,2,3-triazolo[4,5-c][1]benzazepine, a prodrug thereof, or a pharmaceutically acceptable salt thereof to a mammal.

In another embodiment of the present invention, there is provided a method for the prophylaxis or treatment of allergic ophthalmic diseases or allergic nasal diseases, which comprises administering a prophylactically or therapeutically effective amount of 2-(1-isopropoxycarbonyloxy-2-methylpropyl)-7,8-dimethoxy-4(5H),10-dioxo-2H-1,2,3-triazolo[4,5-c][1]benzazepine or a pharmaceutically acceptable salt thereof to a mammal.

According to the present invention, there is also provided use of 7,8-dimethoxy-4(5H),10-dioxo-1H-1,2,3-triazolo[4,5-c][1]benzazepine, a prodrug thereof, or a pharmaceutically acceptable salt thereof, for the preparation of an agent for use in the prophyraxis allergic ophthalmic diseases or allergic nasal diseases.

According to another aspect of the present invention, there is provided use of 2-(1-isopropoxycarbonyloxy-2-methylpropyl)-7,8-dimethoxy-4(5H),10-dioxo-2H-1,2,3-triazolo[4,5-c][1]benzazepine or a pharmaceutically acceptable salt thereof, for the preparation of a prophylactic or therapeutic agent for allergic ophthalmic diseases or allergic nasal diseases.

Further, the present invention can be regarded as follows: (1) a prophylactic or therapeutic agent for allergic ophthalmic diseases or allergic nasal diseases, comprising 7,8-dimethoxy-4(5H),10-dioxo-1H-1,2,3-triazolo[4,5-c][1]benzazepine, or a pharmaceutically acceptable salt thereof; (2) a prophylactic or therapeutic agent for allergic ophthalmic diseases or allergic nasal diseases, comprising 2-(1-isopropoxycarbonyloxy-2-methylpropyl)-7,8-dimethoxy-4(5H),10-dioxo-2H-1,2,3-triazolo[4,5-c][1]benzazepine or a pharmaceutically acceptable salt thereof; (3) the prophylactic or therapeutic agent for allergic ophthalmic diseases according to the above item (1) or (2), which is administered as ocular instillation; (4) the prophylactic or therapeutic agent for allergic nasal diseases according to the above item (1) or (2), which is administered as nasal drops.

The pharmaceutical composition for use in the prophylaxis or treatment of allergic ophthalmic diseases or allergic nasal diseases according to the present invention has few side effects and has potent prophylactic effect and therapeutic effect in late phase where the resistant to therapy against existing eye drops or nasal drops develops.

DETAILED DESCRIPTION OF THE INVENTION

Compound

Compound A (7,8-dimethoxy-4(5H),10-dioxo-1H-1,2,3-triazolo[4,5-c][1]benzazepin e) as an active ingredient in the present invention is a conventional compound and can be produced, for example, by the description on a production process of the compound and the description of Example 43 in the above-described WO 95/18130.

The active ingredient in the present invention may be a prodrug of compound A or a pharmaceutically acceptable salt of the compound or a prodrug thereof. The prodrug of compound A is of such a type that a 1,2,3-triazole group in compound A has been modified, and can be produced according to the above-described WO 99/16770.

A prodrug, which is preferred in the present invention, is compound B (2-(1-isopropoxycarbonyloxy-2-methylpropyl)-7,8-dimethoxy-4(5H),10-dioxo-2H-1,2,3-triazolo[4,5-c][1]benzazepine) and can be produced, for example, by the description described in Example 20 of the above-described WO 99/16770.

In the present invention, compound A or compound B as the active ingredient may be converted to a pharmaceutically acceptable salt thereof which may be used as the active ingredient. Pharmaceutically acceptable salts of compound A or compound B include medically acceptable nontoxic salts. Suitable nontoxic salts include alkali metal or alkaline earth metal salts such as sodium, potassium or calcium salts; hydrohalogenic acid salts such as hydrofluoride salts, hydrochloride salts, hydrobromide salts, or hydroiodide salts; inorganic acid salts such as nitric acid salts, perchloric acid salts, sulfuric acid salts, or phosphoric acid salts; lower alkylsulfonic acid salts such as methanesulfonic acid salts, trifluoromethanesulfonic acid salts, or ethanesulfonic acid salts ("lower alkyl" is preferably C1-3 alkyl); arylsulfonic acid salts such as benzenesulfonic acid salts or p-toluenesulfonic acid salts; organic acid salts such as fumaric acid salts, succinic acid salts, citric acid salts, tartaric acid salts, oxalic acid salts, or maleic acid salts; and amino acid salts such as glutamic acid salts or aspartic acid salts.

Pharmaceutical Composition

As demonstrated in working examples, topical administration (instillation) of compound A as an active ingredient in the present invention to an experimental animal actually showed prophylactic and therapeutic effects against allergic ophthalmic diseases, particularly allergic conjunctivitis. This effect is significantly superior to existing medicaments and can also inhibit late phase allergic reaction (Test Examples 1 and 2). Further, when compound A and compound B were administered as ocular instillation, the concentration of compound A and compound B could be maintained topically for a longer period of time at a higher concentration than that in the oral administration (Test Example 3). Topical administration (rhinenchysis) of compound A to an experimental animal actually showed prophylactic and therapeutic effects on allergic nasal diseases, particularly allergic rhinitis. This effect was significantly superior to existing medicaments (Test Examples 4-1, 4-2 and 5). When compound A and compound B were administered as nasal drops and oral administration, the rhinenchysis could realize a higher inhibitory effect at a lower dose (particularly Test Examples 4-2 and 4-3).

WO 99/16770 shows that compound B is a prodrug of compound A.

Further, from the viewpoint of safety, as compared with the oral administration, in the topical administration (instillation/rhinenchysis), the expose to the whole body is lower, and a potent action is developed at a much lower dose, suggesting that the systemic side effect could be significantly reduced. Further, the results of topical irritation tests show that the safety of compound A and compound B is high. Specifically, toxicity against epithelial cells of cornea in human eyes was studied. As a result, for the 24-hr cell survival rate, any toxicity was not observed in the concentration range of 100 nM to 0.3 mM. This concentration is not less than 60 times higher than the maximum eye tissue concentration 1.29 µg/g (4.7 µM) in the case of instillation of a 0.1% liquid at which compound A develops a satisfactory effect. Even when a severe eye irritation test using rabbits in which instillation is carried out six times per day at 30 min intervals for two days, is carried out, the results are such that, for 3% compound A and 1% compound B, only slight reddening of the conjunctiva was observed and, for 0.5% compound A, irritation was not observed at all, indicating that these compounds are highly safe medicaments.

Accordingly, the active ingredient in the present invention develops an excellent prophylactic or therapeutic effect on allergic ophthalmic diseases or allergic nasal diseases, preferably upon topical application. As described above, according to the present invention, there is provided a pharmaceutical composition for use in the prophylaxis or treatment of allergic ophthalmic diseases or allergic nasal diseases, comprising compound A, a prodrug thereof, or a pharmaceutically acceptable salt thereof, or compound B, or a pharmaceutically acceptable salt thereof.

Allergic ophthalmic diseases include, for example, seasonal allergic conjunctivitis, chronic allergic conjunctivitis, vernal conjunctivitis, atopic keratoconjunctivitis, and giant papillary conjunctivitis.

Allergic nasal diseases include, for example, seasonal allergic rhinitis, chronic allergic rhinitis, allergic sinusitis, and pollinosis.

The pharmaceutical composition for use in the prophylaxis or treatment of allergic ophthalmic diseases according to the present invention may be any pharmaceutical composition so far as it can be topically administered, for example, to ocular-mucous membranes. The pharmaceutical composition according to the present invention is preferably administered as ocular instillation. The topical administration, particularly instillation, can advantageously highly inhibit an inflammatory reaction in a conjunctiva which is a target organ in allergic ophthalmic diseases. Accordingly, the pharmaceutical composition according to the present invention is preferably used in an eye drop form.

When the pharmaceutical composition for use in the prophylaxis or treatment of allergic ophthalmic diseases is administered as ocular instillation, the pharmaceutical composition can be formulated into an eye drop according to a conventional method by mixing the pharmaceutical composition with pharmaceutically acceptable carriers, excipients, and diluents which are already known per se.

In the present invention, the pharmaceutically acceptable carrier, the excipient and the diluent are sometimes collectively referred to as a pharmaceutically acceptable carrier.

When the composition for use in the prophylaxis or treatment of allergic ophthalmic diseases according to the present invention is used as an eye drop, the pharmaceutical composition may be provided in any form which is commonly used as the eye drop. For example, the eye drop may be provided in the form of aqueous eye drops such as aqueous eye drop liquids, aqueous suspension eye drop liquids, viscous eye drop liquids, and solubilized eye drop liquids, and nonaqueous eye drops such as nonaqueous eye drop liquids and nonaqueous suspension liquids. In the present invention, aqueous eye drop liquids are more preferred.

When the pharmaceutical composition for use in the prophylaxis or treatment of allergic ophthalmic diseases is formulated, for example, into aqueous eye drop liquids, various additives commonly used in aqueous eye drop liquids may be properly incorporated in the aqueous eye drop liquids. Additives include buffering agents, tonicity adjusting agents, antiseptics, preservatives, solubilizers (stabilizers), pH adjustors, thickeners, and chelating agents.

The pharmaceutical composition for use in the prophylaxis or treatment of allergic nasal diseases according to the present invention may be any pharmaceutical composition so far as it can be topically administered, for example, to nasal mucosa. The pharmaceutical composition according to the present invention is preferably administered as nasal drops. The topical administration, particularly rhinenchysis, can advantageously highly inhibit an inflammatory reaction in a nasal mucosa which is a target organ in allergic nasal diseases. Accordingly, the pharmaceutical composition according to the present invention is preferably used in a nasal drop form.

When the pharmaceutical composition for use in the prophylaxis or treatment of allergic nasal diseases is administered as nasal drops, the pharmaceutical composition can be formulated into a nasal drop according to a conventional method by mixing the pharmaceutical composition with pharmaceutically acceptable carriers, excipients, and diluents which are already known per se.

When the composition for use in the prophylaxis or treatment of allergic nasal diseases according to the present invention is used as a nasal drop, the pharmaceutical composition may be provided in any form which is commonly used as the nasal drop. For example, the nasal drop may be provided in the form of nasal drops such as aqueous nasal drop liquids, aqueous suspension nasal drop liquids, nonaqueous nasal drop liquids, nonaqueous suspension nasal drop liquids, or gel nasal drop liquids.

When the pharmaceutical composition for use in the prophylaxis or treatment of allergic nasal diseases is formulated, for example, into nasal drops, various additives commonly used in nasal drops may be properly incorporated in the nasal drop. Additives include buffering agents, tonicity adjusting agents, preservatives, solubilizers (stabilizers), pH adjustors, thickeners, and chelating agents.

Buffering agents usable in the present invention include, for example, borate buffering agents, phosphate buffering agents, citrate buffering agents, tartrate buffering agents, and acetate buffering agents.

Tonicity adjusting agents include, for example, salts such as sodium chloride, saccharides such as sorbitol, mannitol, and glucose, polyhydric alcohols such as glycerin, polyethyleneglycol, and propylene glycol.

Antiseptics include, for example, benzalkonium chloride, benzethonium chloride, and paraoxybenzoic acid esters such as methyl p-oxybenzoate and ethyl p-oxybenzoate.

Preservatives include p-hydroxybenzoic esters and benzalkonium chloride.

pH adjustors include, for example, sodium hydroxide, ammonium hydroxide, hydrochloric acid, acetic acid, and phosphoric acid.

Thickeners include, for example, methylcellulose, carboxymethylcellulose, hydroxypropyl methylcellulose, polyvinyl alcohol, polyvinylpyrrolidone, and polyacrylic acid and its salt.

They may be used in a combination of two or more.

When the pharmaceutical composition for use in the prophylaxis or treatment of allergic ophthalmic diseases is used as an ophthalmic ointment, purified lanolin, vaseline, plastibase, and liquid paraffin may be properly used as bases for the ophthalmic ointment.

In the pharmaceutical composition for use in the prophylaxis or treatment of allergic ophthalmic diseases or allergic nasal diseases, the active ingredient according to the present invention may be properly used in combination with other opthalmological chemical agents, for example, chlorpheniramine maleate, naphazoline hydrochloride, sodium azulene sulfonate, lysozyme chloride, and glycyrrhetinic acid, or chemical agents for treating nasal diseases, so far as the contemplated object can be attained.

The dose of the pharmaceutical composition according to the present invention may be properly varied depending upon the amount of the active ingredient contained in the pharmaceutical composition. For preventing or treating allergic ophthalmic diseases or allergic nasal diseases as the target disease, a prophylactically or therapeutically effective amount of the active ingredient is administered to a patient.

The expression "prophylactically or therapeutically effective amount" means such an amount that a prophylactic or therapeutic effect can be attained in a patient suffering from the target allergic ophthalmic disease or allergic nasal disease. In general, the effective amount can be appropriately determined in consideration of particular conditions, for example, the age, weight, sex, type of disease, and severity of condition of patients.

In the present invention, when compound A is used, the amount of compound A used may be any amount, so far as the contemplated effect can be attained, and may vary depending, for example, upon the symptom and age. The amount of compound A is preferably 0.001 to 3% by weight, more preferably 0.01 to 1% by weight. For ophthalmic administration (instillation), compound A may be administered, for example, by eye dropping twice to four times per day by one to a few drops at a time. When the level of severity is higher, compound A may be administered, for example, as ocular instillation a few times per day. The instillation dose is typically about 30 μL. For rhinenchysis, compound A may be administered, for example, by nasal dropping or by spray from a spray bottle filled with compound A at a dose of 10 to 200 μL at a time, once to four times per day.

In the present invention, when compound B is used, the amount of compound B used may be any amount, so far as the contemplated effect can be attained, and may vary depending, for example, upon the symptom and age. The amount of compound B is preferably 0.001 to 3% by weight, more preferably 0.01 to 1% by weight. For instillation, compound B may be administered, for example, by eye dropping twice to four times per day by one to a few drops at a time. When the level of severity is higher, compound B may be administered, for example, as ocular instillation a few times per day. The instillation dose is typically about 30 μL. For rhinenchysis, compound B may be administered, for example, by nasal dropping or by spray from a spray bottle filled with compound B at a dose of 10 to 200 μL at a time, once to four times per day.

The pharmaceutical composition for use in the prophylaxis or treatment of allergic ophthalmic diseases or allergic nasal diseases may fall within a pH range which is commonly used as eye drops or nasal drops, and is preferably in the range of 4.0 to 8.0.

EXAMPLES

The present invention is further illustrated by the following Examples that are not intended as a limitation of the invention.

Test Example 1

Prophylactic Effect on Allergic Conjunctivitis

Test Example 1-1

Prophylactic Effect of Compound A on Allergic Conjunctivitis

Male SD rats were prepared. *Bordetella pertussis* ($4 \times 10^{10}$) and 1 mg of dinitrophenylated ovalbumin (hereinafter often abbreviated to "DNP-OA") were subcutaneously administered into the footpad of the rats. After 8 to 10 days from the administration, a 3% DNP-OA solution was administered to the right eye of the rats to induce an allergic reaction. In some experiments, in order to confirm dye leakage and location of edema, a dye was injected, and, in the anatomy, the coincidence of dye leakage with the location of edema was confirmed. Evans Blue (a dye) (25 mg/kg) was intravenously administered six hr after the induction of the allergic reaction.

After 9 hr from the induction of the allergic reaction, the eyeballs of the rats were harvested. Further, lenses, hydatoids, and the contents of the vitreous body were removed from the eyeballs, and the weight of the tissues was measured. Furthermore, the dye leakage amount in the harvested eye tissue was measured. For dye measurement, the eye tissue was immersed in 0.15 mL of 1 N KOH and was lysed at 37° C. for two or three days. A 0.6 N phosphoric acid/acetic acid mixed liquid (0.9 mL) was added to the lysed tissue, and the mixture was centrifuged at 1750 g for 15 min. The absorbance (630 nm) of Evans Blue in the supernatant was measured with Multiskan JX (manufactured by Labsystem Ltd.). The amount of the dye was regarded as a dye leakage amount.

Compound A was dissolved in 0.15 M sodium hydrogencarbonate, and the solution was adjusted to pH 7.2. For the control group, 0.15 M sodium hydrogencarbonate adjusted to pH 7.2 was administered. For a negative control group (a nonsensitization group), a 3% DNP-OA solution was administered to the right eye of the nonsensitized rats, and the solvent was used into the same manner as in the control group.

The medicament or the solvent was administered to the right eye (5 μL/eye) 15 min before the induction of the allergic reaction. Compound A was administered at concentrations of 0.01%, 0.1%, and 1% for studies of dose response.

The results are shown as in Table 1.

In the table, the inhibition ratio was calculated by the following equation.

$$\text{Inhibition}(\%) = 100 \times \{(B-A)-(C-A)\} \div (B-A)$$

wherein A represents a negative control group (a nonsensitized group); B represents a control group; and C represents a medicament administered group.

TABLE 1

Prophylactic effect of compound A on allergic conjunctivitis (studies on dose response)

| Medicament | Dose/rat | Medicament concentration | Inhibition ratio (%) Increase in tissue weight | Increase in dye leakage amount |
|---|---|---|---|---|
| Compound A | 0.05 μg/rat | 0.01% | 67.0% ** | 74.4% ** |
| Compound A | 0.5 μg/rat | 0.1% | 89.0% ** | 83.9% ** |
| Compound A | 5 μg/rat | 1% | 83.7% ** | 87.6% ** |

** $p < 0.01$ compared to control group (Dunnett's multiple comparison test)
(tissue weight for nonsensitized group: 76.4 ± 2.5 mg, tissue weight for control group: 114.2 ± 4.7 mg, n = 8)
(dye leakage amount for nonsensitized group: 2.96 ± 0.17 mg, dye leakage amount for control group: 6.91 ± 0.47 mg, n = 8)

As shown in the results, it was confirmed that the dye leakage amount substantially correlated with the tissue weight, the dye leakage site and the edema could be visually observed to be concentrated on the conjunctiva. In the anatomy, the leakage of the dye was concentrated in the conjunctiva, and, based on this fact, it was determined that the allergic reaction is mainly induced in the conjunctiva. The weight of the eye tissue, which has induced the allergic reaction, increases by edema mainly developed in the conjunctiva. Accordingly, in the following tests, the effect of the medicament will be examined using an increase in eye tissue weight as an index of the late phase.

Test Example 1-2

Comparison of Prophylactic Effect on Allergic Conjunctivitis Between Compound A and Existing Medicaments A comparison test for prophylactic effect on allergic conjunctivitis was carried out between compound A and existing medicaments. For comparison, the following existing medicaments for allergic conjunctivitis (commercially available eye drops) were used.

1) Mast cell stabilizer (histamine release inhibitor): Cromoglycate (cromoglycate sodium, manufactured by Astellas Pharma Inc.)

2) Antihistamine agent: Ketotifen (ketotifen fumarate, manufactured by Novartis) and Levocabastine (levocabastine hydrochloride, manufactured by Santen Pharmaceutical Co., Ltd.)

3) Steroid: Betamethazone (betamethazone sodium phosphate, manufactured by Shionogi & Co., Ltd.) and Fluorometholone (fluorometholone, manufactured by Santen Pharmaceutical Co., Ltd.)

Compound A and existing medicaments were administered at concentrations shown in Table 2, and the prophylactic effect on the allergic conjunctivitis was confirmed in the same manner as in Test Example 1-1.

The results were as shown in Table 2.

TABLE 2

Comparison of prophylactic effect on allergic conjunctivitis between compound A and existing medicaments

| Medicament | Medicament concentration | Inhibition ratio Increase in tissue weight |
|---|---|---|
| Compound A | 0.1% | 99.1% ** |
| Levocabastine | 0.025% | 11.1% |
| Ketotifen | 0.05% | 13.4% |
| Cromoglycate | 2% | 14.7% |
| Betamethazone | 0.1% | 79.6% ** |
| Fluorometholone | 0.1% | 59.4% * |

*, ** compared to control group $p < 0.05, 0.01$ (Dunnett's multiple comparison test)

As shown in the results, existing medicaments for allergic conjunctivitis (commercially available eye drops) except for steroid did not inhibited late phase allergic reaction.

Test Example 2

Therapeutic Effect of Compound A on Allergic Conjunctivitis (Studies on Dose Response)

In clinical practice, in most cases, a medicament is generally administered after the onset of a symptom. Accordingly, a test was carried out on therapeutic effect of compound A on allergic conjunctivitis.

As can be seen from the results of Test Example 1-2, existing eye drops for allergic conjunctivitis except for steroid did not inhibit the late phase allergic reaction. Accordingly, for the therapeutic effect (effect on the medicament administration after the onset), the results only for Betamethasone which had exhibited prophylactic effect in Test Example 1-2 were evaluated for comparison.

Compound A, Betamethasone, control group, and negative control group were administered at the same concentration as in Test Example 1-1, and the concentration of Betamethasone was as shown in Table 3.

The test was carried out in the same manner as in Test Example 1-1, except that, three hr after the induction of the allergic reaction, for compound A, Betamethasone, control group, and negative control group were administered, the test solution was administered at a dose of 5 μL/eye to the right eye.

The results were as shown in Table 3.

TABLE 3

Therapeutic effect of compound A on allergic conjunctivitis

| Medicament | | Tissue weight increase |
|---|---|---|
| Compound A | 0.01% | 70.3% ** |
| Compound A | 0.1% | 99.9% ** |
| Compound A | 1% | 103.7% ** |
| Betamethasone | 0.1% | 74.8% ** |

** $p < 0.01$ compared to control group (Dunnett's multiple comparison test)

As shown in Table 3, compound A and Betamethasone had potent therapeutic effect on allergic conjunctivitis.

Test Example 3

Change in Concentration of Administered Compound A and Compound B in the Eye Tissue Test Example 3-1

Change in Concentration of Ophthalmically Administered Compound A and Compound B in the Eye Tissue A test solution (0.1% or 1%) of compound A in an isotonic borate buffer solution adjusted to pH 7.4 and a test solution (0.1%) of compound B in an isotonic borate buffer solution were provided, and 50 μL of each test solution was administered as ocular instillation to male rabbits.

The concentration of compound A in the eye tissue after instillation was measured as follows. At the outset, the tissue was removed from the test animals and was cryopreserved. Purified water (0.1 mL) was added to a sufficient quantity of the cryopreserved tissue and the like followed by homogenization. Thereafter, 0.5 mL of 0.1% phosphoric acid, 0.05 mL of an internal standard solution (a predetermined internal standard substance (10.1 μL/mL) described in WO 95/18130), 0.05 mL of acetonitrile, and 0.05 mL of purified water were added thereto. An extraction solvent (25% chloroform/diethyl ether) (8 mL) was added, and the mixture was shaken and centrifuged. Thereafter, 7 mL of the organic layer was evaporated to dryness under the negative pressure, and the residue was dissolved in 0.3 mL of a mobile phase to give an analyte. A liquid prepared by mixing and dissolving 0.55 g of tetraoxyl ammonium bromide into 450 mL of acetonitrile, 450 mL of 10 mM phosphate buffer solution, and 100 mL of methanol was used as the mobile phase. The concentration of compound A was measured by injecting 0.025 mL of the analyte into high-performance liquid chromatography (HPLC) (measurement conditions: fluorescence excitation 270 nm, emission 466 nm).

The concentration of only compound A in the eye tissue was measured because compound B is a prodrug of compound A.

The results were as shown in Table 4.

TABLE 4

Change in concentraion of compound A in the eye tissue

| | Administered medicament and its concentration | | Time after instillation (hr) | | | | | |
|---|---|---|---|---|---|---|---|---|
| | Medicament | Concentration (%) | 0.25 | 1 | 2 | 4 | 8 | 24 |
| Concentration | Compound A | 0.1% | 1.29 ± 0.71 | 0.05 ± 0.01 | 0.15 ± 0.11 | 0.04 ± 0.07 | 0.07 ± 0.08 | 0 |
| in the eye | Compound A | 1% | 6.09 ± 2.20 | 1.15 ± 0.83 | 1.26 ± 0.94 | 1.38 ± 0.54 | 0.66 ± 0.42 | 0.06 ± 0.06 |
| tissue (μg/g) | Compound B | 0.1% | 0.82 ± 0.31 | 0.11 ± 0.04 | 0.30 ± 0.93 | 0.04 ± 0.01 | 0.07 ± 0.07 | 0.01 ± 0.01 |

In the table, the numerals are avarage ± standard error.

Test Example 3-2

Change in Concentration of Orally Administered Compound B in the Plasma and the Eye Tissue Compound B was suspended in 1% hydroxymethylcellulose to regulate the concentration of compound to 0.2 mg/mL. This test solution was orally administered to male rats at a dose of 5 mL/kg (dose: 1 mg/kg (200 µg/rat). The concentration profile of compound A after the oral administration in plasma and the eye tissue was measured.

The results were as shown in Table 5.

TABLE 5

Change in concentration of compound A in the plasma and the eye tissue after oral administration of compound B

| Concentration in tissue | Time after oral administration (hr) | | | |
|---|---|---|---|---|
| | 0.5 | 2 | 8 | 24 |
| Plasma concentration (µg/mL) | 0.027 | 0.018 | 0.001 | 0 |
| Eye tissue concentration (µg/g) | 0.002 | 0.0015 | N.D. | N.D. |

In the table, numerals are mean. N.D.: Not detected

As can be seen from the results shown in Tables 4 and 5, as compared with the case where compound B was orally administered, the ophthalmic administration of compound A and compound B could maintain the concentration of compound A in the eye tissue at a far higher concentration for a far longer period of time (8 hr or more).

Formulation Example

Prophylactic or Therapeutic Agent for Allergic Ophthalmic Diseases

General methods for producing pharmaceutical preparations as prophylactic or therapeutic agents of allergic ophthalmic diseases and production example of the pharmaceutical preparations according to the present invention will be described.

Compound A or compound B and a tonicity adjusting agent were added to sterilized purified water. If necessary, for example, a preservative, a buffering agent, a stabilizer, and a thickener were added to and dissolved in the solvent. Specific formulation examples are shown below.

Production Example 1

Solution Formulation for Topical Opthalmologic Administration

TABLE 6

| Ingredients | Concentration (w/v %) |
|---|---|
| Compound A | 0.1 |
| Boric acid | 0.0006 |
| Sodium chloride (tonicity adjusting agent) | q.s. |
| Benzalconium chloride | 0.005 |
| Hydrochloric acid (pH adjustor) | q.s. pH 7.0 |
| Purified water | q.s. |

Production Example 2

Suspension Formulation for Topical Opthalmologic Administration

TABLE 7

| Ingredients | Concentration (w/v %) |
|---|---|
| Compound B | 0.1 |
| Hydroxypropylmethylcellulose | q.s. |
| Boric acid | 0.0006 |
| Polysorbate 80 | 0.01 |
| Benzalconium chloride | 0.005 |
| Hydrochloric acid (pH adjustor) | q.s. pH 7.0 |
| Purified water | q.s. |

Test Example 4

Prophylactic Effect on Allergic Rhinitis

Test Example 4-1

Prophylactic Effect of Compound A on Allergic Rhinitis (Studies on Dose Response)

Male Sprague Dawley rats (n=6) were prepared. *Bordetella pertussis* ($4 \times 10^{10}$) and 1 mg of dinitrophenylated ovalbumin (hereinafter referred to as "DNP-OA") were subcutaneously administered into the footpad of the rats. After nine days from the administration, 15 µL of a 13.3% DNP-OA solution was administered into both nasal cavities to induce an allergic reaction. After six hr from the antigen administration, Evans Blue (a dye) (50 mg/kg) was intravenously administered.

After nine hr from the induction of the allergic reaction, the nasal septal mucosa of the rats was harvested, and the weight of the tissue was measured. The tissue of the nasal septal mucosa was lysed with 1 N KOH, and the leakage amount of the dye was determined as an index of vascular permeability in the late phase of the allergic rhinitis.

Compound A was dissolved in physiological saline. For the control group not subjected to any medicament treatment, the physiological saline used in the solvent for compound A was used. The negative control group which had not induced the allergy was regarded as a saline group. In this case, physiological saline was administered instead of the antigen. Compound A and the control group (physiological saline) (each 5 µL) were administered as nasal drops into both nasal cavities, immediately before the induction of the allergic reaction. Compound A was administered at concentrations of 0.01%, 0.1%, and 1% to study the dose response.

The results were as shown in Table 8.

In the table, the inhibition ratio was calculated by the following equation.

$$\text{Inhibition}(\%) = 100 \times \{(B-A)-(C-A)\} \div (B-A)$$

wherein A represents a negative control group (a nonsensitized group); B represents a control group; and C represents a medicament administered group.

TABLE 8

Prophylactic effect of compound A on allergic rhinitis

| Medicament | Dose/rat | Medicament concentration | Increase in dye leakage amount Inhibition ratio |
|---|---|---|---|
| Compound A | 1 μg/rat | 0.01% | 52.9% ** |
| Compound A | 10 μg/rat | 0.1% | 111.7% ** |
| Compound A | 100 μg/rat | 1% | 123.1% ** |

** $p < 0.01$ compared to control group (Dunnett's multiple comparison test)

The medicament was administered immediately before the antigen administration (start of allergy).

The results show that, when compound A is prophylactically administered as nasal drops, compound A is effective against allergic rhinitis dose-dependently.

Test Example 4-2

Comparison Between Compound A and Existing Medicaments on Prophylactic Effect on Allergic Rhinitis A test on comparison between compound A and existing medicaments for prophylactic effect on allergic rhinitis. For comparison, existing medicaments for allergic rhinitis (commercially available nasal drops) were used.

1) Mast cell stabilizer (histamine release inhibitor): Cromoglycate (cromoglycate sodium, manufactured by Astellas Pharma Inc.) and Amlexanox (manufactured by Takeda Chemical Industries, Ltd.)

2) Antihistamine agent: Ketotifen (ketotifen fumarate, manufactured by Novartis) and Levocabastine (levocabastine hydrochloride, manufactured by NIPPON SHINYAKU CO., LTD.)

3) Steroid: Fluticasone propionate (fluticasone propinate, manufactured by Glaxo SmithKline K.K.)

Compound A and existing medicaments were administered at concentrations shown in Table 9 immediately before the antigen administration (start of allergy), and the prophylactic effect on the allergic conjunctivitis was confirmed in the same manner as in Test Example 4-1.

The results were as shown in Table 9.

TABLE 9

Comparison between compound A and existing medicaments for prophylactic effect on allergic rhinitis

| Medicament | Dose/rat | Medicament concentration | Increase in dye leakage amount Inhibition ratio |
|---|---|---|---|
| Compound A | 10 μg/rat | 0.1% | 95.7% ** |
| Cromoglycate | 200 μg/rat | 2% | 2.9% |
| Amlexanox | 25 μg/rat | 0.25% | 81.1% ** |
| Levocabastine | 2.5 μg/rat | 0.025% | 22.7% |
| Ketotifen | 5.5 μg/rat | 0.055% | 49.4% |
| Fluticasone | 5.1 μg/rat | 0.051% | 106.0% ** |

** $p < 0.01$ compared to control group (Dunnett's multiple comparison test)

As can be seen from the results, compound A, Amlexanox, and Ketotifen had prophylactic effect on allergic rhinitis.

Test Example 4-3

Prophylactic Effect of Compound B Against Allergic Rhinitis where Compound B was Orally Administered The prophylactic effect of compound B on allergic rihinitis in the same manner as in Test Example 4-1, except that compound B was suspended in hydroxypropylmethylcellulose and the suspension was orally administered. The medicament was administered 15 min before the administration of the antigin (start of allergy).

The results were as shown in Table 10.

TABLE 10

| Medicament | Dose/rat | Dose (mg/kg) | Increase in dye leakage amount Inhibition ratio |
|---|---|---|---|
| Compound B | 200 μg/rat | 1 mg/kg | 46.3% ** |
| Compound B | 1000 μg/rat | 5 mg/kg | 81.9% ** |

** Compared to control group $p < 0.01$ (Dunnett's multiple comparison test)

As can be seen from Tables 9 and 10, when compound B is assumed to be converted as it is to compound A in vivo, it can be said that the rhinenchysis exhibited a higher inhibition ratio at a lower dose. Accordingly, it could be expected that, when compound A is formulated into nasal drops, more reliable drug efficacy can be provided at a concentration of not less than 0.1% and, further, a reduction in total exposure can reduce systemic side effect.

Test Example 5

Therapeutic Effect of Compound A on Allergic Rhinitis

In clinical practice, it is important that the effect can be attained also in such a state that a symptom is developed. Accordingly, a test was carried out on the therapeutic effect of compound A on allergic rhinitis. For comparison, Amlexanox and Ketotifen, which were effective on prophylactic effect in Test Example 3-2, were also evaluated.

In the same manner as in Test Example 4-1, the allergic reaction was induced, and the vascular permeability in the late phase of the allergic rhinitis was measured. In this case, however, for the evaluation of the therapeutic effect, compound A, Amlexanox, and Ketotifen were administered one hr after the induction of the allergic reaction. Since greenie was leaked, the dose was doubled (10 μL) so that the dispersion of the medicament within the nasal cavities is not inhibited, and the concentration of the medicament was regulated with physiological saline to the half of the concentration in the experiment on prophylactic effect to render the dose per individual identical.

The results were as shown in Table 11.

TABLE 11

Therapeutic effect of compound A on allergic rhinitis

| Medicament | Dose/rat | Medicament concentration | Dye leakage amount increase Inhibition ratio |
|---|---|---|---|
| Compound A | 10 μg/rat | 0.05% | 93.8% ** |
| Amlexanox | 25 μg/rat | 0.125% | 25.0% |
| Ketotifen | 5.5 μg/rat | 0.0275% | 48.6% |

$p < 0.01$ compared to control group (Dunnett's multiple comparison test)

The medicament was administered one hr after the administration of the antigen.

From the results, the administration of compound A as nasal drops exhibited therapeutic effect on the allergic rhinitis.

Formulation Example

Prophylactic or Therapeutic Agent for Allergic Nasal Diseases

General methods for producing prophylactic or therapeutic agents for allergic nasal diseases and production examples of the prophylactic or therapeutic agents for allergic nasal diseases according to the present invention will be described.

Compound A or compound B and a tonicity adjusting agent are added to sterilized purified water. If necessary, for example, a preservative, a buffering agent, a stabilizer, and a thickening agent were added to and dissolved in a solvent. Specific formulation examples will be described below.

Production Example 3

Topical Solution Formulation for Nasal Diseases

TABLE 12

| Ingredient | Concentration (w/v %) |
| --- | --- |
| Compound A | 0.1 |
| Boric acid | 0.0006 |
| Sodium chloride (tonicity adjusting agents) | q.s. |
| Benzalconium chloride | 0.005 |
| Hydrochloric acid (pH adjustor) | q.s. pH 7.0 |
| Purified water | q.s. |

Production Example 4

Topical Suspension Formulation for Nasal Diseases

TABLE 13

| Ingredients | Concentration (w/v %) |
| --- | --- |
| Compound B | 0.1 |
| Hydroxypropylmethylcellulose | q.s. |
| Boric acid | 0.0006 |
| Polysorbate 80 | 0.01 |
| Benzalconium chloride | 0.005 |
| Hydrochloric acid (pH adjustor) | q.s. pH 7.0 |
| Purified water | q.s. |

The invention claimed is:

1. A method for the treatment of allergic ophthalmic diseases or allergic nasal diseases, which comprises administering a therapeutically effective amount of 7,8-dimethoxy-4 (5H),10-dioxo-1H-1,2,3-triazolo[4,5-c][1]benzazepine or a pharmaceutically acceptable salt thereof to a mammal.

2. A method for the treatment of allergic ophthalmic diseases or allergic nasal diseases, which comprises administering a therapeutically effective amount of 2-(1-isopropoxycarbonyloxy-2-methylpropyl)-7,8-dimethoxy-4(5H),10-dioxo-2H-1,2,3-triazolo[4,5-c][1]benzazepine or a pharmaceutically acceptable salt thereof to a mammal.

3. The method according to claim 1, wherein the compound is administered by instillation.

4. The method according to claim 1, wherein the compound is administered as nasal drops.

5. The method according to claim 1, comprising administering an effective amount of a compound together with a pharmaceutically acceptable carrier.

6. The method according to claim 2, wherein the compound is administered by instillation.

7. The method according to claim 2, wherein the compound is administered as nasal drops.

8. The method according to claim 2, comprising administering an effective amount of a compound together with a pharmaceutically acceptable carrier.

9. The method according to claim 3, comprising administering an effective amount of a compound together with a pharmaceutically acceptable carrier.

10. The method according to claim 4, comprising administering an effective amount of a compound together with a pharmaceutically acceptable carrier.

* * * * *